United States Patent [19]

Bhinde et al.

[11] Patent Number: 5,723,697
[45] Date of Patent: Mar. 3, 1998

[54] CATALYTIC OXIDATION OF LIGHT ALKANES IN PRESENCE OF A BASE

[75] Inventors: Manoj V. Bhinde, Boothwyn; Thomas W. Bierl, West Chester, both of Pa.

[73] Assignee: Sun Company, Inc. (R&M), Philadelphia, Pa.

[21] Appl. No.: 580,918

[22] Filed: Dec. 29, 1995

[51] Int. Cl.[6] ................................................ C07C 29/50
[52] U.S. Cl. .................................. 568/910; 568/910.5
[58] Field of Search .............................. 568/910, 910.5

[56] References Cited

U.S. PATENT DOCUMENTS

| | | | |
|---|---|---|---|
| 3,816,548 | 6/1974 | Williams et al. | 568/910 |
| 4,028,423 | 6/1977 | Brownstein et al. | 568/910 |

*Primary Examiner*—C. Warren Ivy
*Assistant Examiner*—Lyman H. Smith
*Attorney, Agent, or Firm*—Stephen T. Falk; Q. Todd Dickinson

[57] ABSTRACT

The presence of a base in the reaction mixture in a metal-ligand catalyzed partial oxidation of alkanes results in sustained catalyst activity, and in greater percent conversion as compared with oxidation in the absence of base, while maintaining satisfactory selectivity for the desired oxidation, for example the oxidation of isobutane to isobutanol.

28 Claims, 1 Drawing Sheet

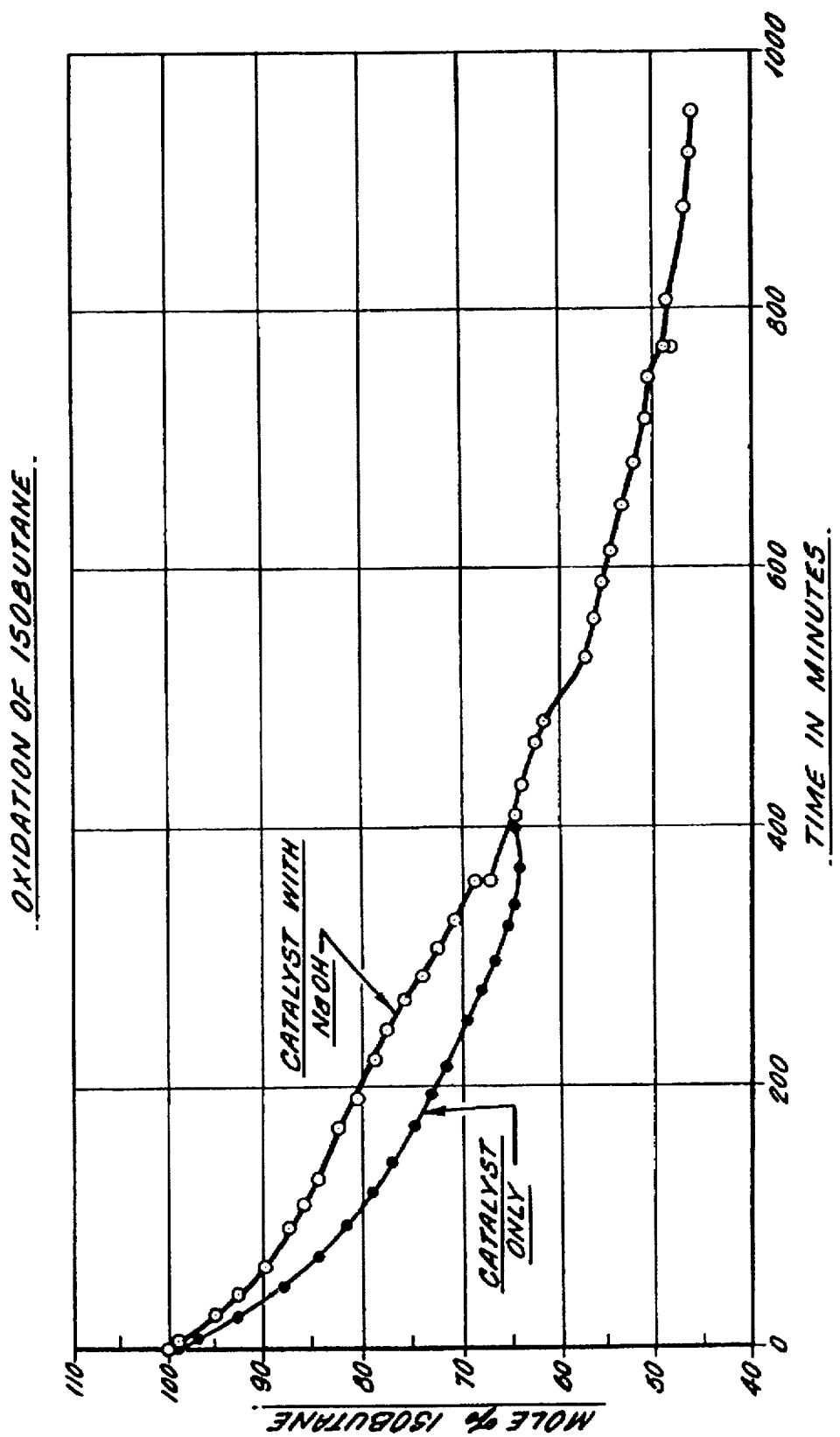

CATALYTIC OXIDATION OF LIGHT ALKANES IN PRESENCE OF A BASE

The Government of the United States of America has rights in this invention pursuant to Cooperative Agreement No. DE-FC21-90MC26029 awarded by the U.S. Department of Energy.

BACKGROUND AND PRIOR ART

Oxidation of alkanes with air or oxygen has been known to occur at 125°–200° C. under vapor phase conditions without catalysts. D. L. Allera, T. Mill, D. C. Hendry and F. R. Mayo, Proceedings of the Oxidation Symposium, National ACS Meeting, San Francisco (1967), pp. I-373–I-396. The major products of reaction are tert-butylalcohol, tert-butylhydroperoxide and acetone.

It is also known that Fe porphyrinato complexes can catalyze oxidation of light alkanes at lower temperatures under liquid phase conditions with resulting >80% selectivity for desired products and conversion of alkanes in the vicinity of 35%. U.S. Pat. No. 4,900,871.

Other metal complexes of organic ligands are known catalysts for oxidation of alkanes and other organic compounds, as disclosed for example in U.S. Pat. Nos. 4,895,680; 4,895,682; 4,970,348; 5,118,886; 5,212,300; 5,120,882; and 5,212,300; each of which is hereby incorporated by reference herein.

DESCRIPTION OF THE INVENTION

In the method of the invention, the presence of a base in the reaction mixture in a metal-ligand catalyzed partial oxidation of alkanes results in sustained catalyst activity, and in greater percent conversion as compared with oxidation in the absence of base, while maintaining satisfactory selectivity for the desired oxidation, for example the oxidation of isobutane to isobutanol. The enhancement of performance resulting from addition of a base may result in substantial cost savings because of process simplification as well as lower catalyst consumption. The increased conversion makes it possible to lower cost by using smaller reactors, separation equipment and recycle streams.

STARTING MATERIAL

The starting material for the process of the invention is an alkane, such as methane, ethane, propane, n-butane, isobutane, n-pentane, isopentane, and the like. Preferably but not necessarily, the starting material contains 1 to 10 carbon atoms in the molecule. Mixtures of compounds can be used.

METAL ORGANIC LIGAND CATALYST

The term "ligand" is used herein in its conventional meaning to refer generically to a group or system of atoms which forms one or more bonds to a metal ion, i.e., forms a coordination complex, and stabilizes this metal coordination complex in desirable oxidation states. The catalyst used in the method of the invention typically comprises a transition metal complex of a ligand selected from the group consisting of porphyrins, phthalocyanines, porphenes, porphycenes, 1,3-bis(arylimino)isoindolines, acetates, Schiff bases such as salen, saleph and the like, mono-, bi-, tri- and tetradentate systems such as acetylacetonates, naphthenates, propanates, butyrates, benzoates, stearates, bipyridines, terpyridines, phenanthrolines, dithiocarbamates, xanthates, salicylaldimines, cyclam, dioxycyclams, pyrazoylborates, and tetraazamacrocycles such as tetramethyltetraazadibenzocycloheptadecane. Preferably the ligand is a porphyrin or a phthalocyanine.

In one embodiment of the invention, the ligand is substituted with electron-withdrawing atoms or groups, such as halogen atoms; e.g., halogenated mono-, di-, tri- and tetradentate systems. Porphyrin catalysts used according to the invention preferably contain electron-withdrawing atoms or groups in meso and/or beta positions. Preferably such atoms or groups comprise halogen, nitro, cyano, halocarbyl, nitrocarbyl and cyanocarbyl atoms or groups. Likewise, phthalocyanine catalysts used according to the invention may be substituted with electron-withdrawing atoms or groups.

In one embodiment of the invention, the ligand is perhalogenated; i.e., all or substantially all, within the tolerances of the catalyst preparation process as practiced by the skilled practitioner, of the available hydrogen atoms on the ligand are substituted with halogen atoms; e.g., Fe(TPFPP)-$\beta$-$Br_8$—Cl, meso-tetra(pentafluorophenyl)-$\beta$-octabromoporphyrinato iron chloride; Fe($Cl$Pc)Cl,perchlorophthalocyanato iron chloride.

Preferably, the metal in the catalyst is iron, cobalt, chromium, manganese, ruthenium or copper. Iron is particularly preferred.

Further discussion on the structure and methods of preparation of such ligand systems may be found in U.S. Pat. Nos. 4,895,680; 4,895,682; 4,970,348; 5,118,886; 5,212,300; 5,120,882; 5,212,300; 5,280,115; 5,345,008; 5,354,857; 5,382,662; and 5,395,988; each of which is hereby incorporated by reference herein.

The following is a description of examples of suitable catalysts for use in the process of the invention. It is not intended to limit the scope of the invention.

PORPHYRIN CATALYSTS

Porphyrins may be defined, for example, as compounds comprising four pyrrole rings joined by methylene groups and having in the center a metal atom. R. Grant, et al., eds., *Grant & Hackh's Chemical Dictionary*, 5th ed., New York, 1987. Suitable porphyrin catalysts which may be used as catalysts in the process according to the invention include, for example, the following:

Fe(TPFPP)$Cl_8$OH, mesotetra(pentafluorophenyl)-$\beta$-octachloro porphyrinato iron hydroxide, also referred to herein as Fe[$PPF_{20}Cl_8$]OH, in which "PP" designates"phenylporphyrin";

[Fe(TPP)]$_2$N, meso-tetraphenylporphyrinato iron nitride;

Mn(TPP)$N_3$, meso-tetraphenylporphyrinato manganese azide;

Fe(TPP)OAc, meso-tetraphenylporphyrinato iron acetate;

Fe(TPFPP)Cl, meso-tetra(pentafluorophenyl) porphyrinato iron chloride;

Fe(TPFPP)$N_3$, meso-tetra(pentafluorophenyl) porphyrinato iron azide;

Cr(TPFPP)OH, meso-tetra(pentafluorophenyl) porphyrinato chromium hydroxide;

Fe[(TPFPP)-$\beta$-$(CN)_4$]Cl, meso-tetra(pentafluorophenyl)-$\beta$-tetracyanoporphyrinato iron chloride;

FeP$(CF_3)_4$-$\beta$-$(CN)_4$-$X_4$, meso-tetra(trifluoromethyl)-$\beta$-tetracyano-$\beta$-tetrahaloporphyrinato iron;

Fe[(TPFPP)-$\beta$-$NO_2$]X, meso-tetra(pentafluorophenyl)-$\beta$-nitro-porphyrinato iron halide;

FeP$(NO_2)_4$-$\beta$-$X_8$, meso-tetranitro-$\beta$-octahaloporphyrinato iron;

FeP(CF$_3$)$_4$-β-(NO$_2$)$_4$, meso-tetra(trifluoromethyl)-β-tetranitro-porphyrinato iron;

FeP(CN)$_4$, meso-tetracyanoporphyrinato iron;

Fe(TPFPP)-β-Br$_6$-β-(CN)$_2$,meso-tetra (pentafluorophenyl)-β-hexabromo-β-dicyanoporphyrinato iron;

Fe(TPFPP)-β-Br$_8$—Cl, meso-tetra(pentafluorophenyl)-β-octabromo porphyrinato iron chloride;

FeP(NO$_2$)$_4$Cl, meso-tetranitroporphyrinato iron chloride;

FeP(NO$_2$)$_4$-[β-(Et)$_4$-(CF$_3$)$_4$]Cl, meso-tetranitro-β-tetraethyl β-tetra(trifluoromethyl) porphyrinato iron chloride;

Fe(TPFPP)OH, meso-tetra(pentafluorophenyl) porphyrinato iron hydroxide;

Fe(TPFPP)$_2$(CF$_3$)$_2$, meso-(5,15)-bis(pentafluorophenyl)-meso-(10,20)-bis(trifluoromethyl)porphyrinato iron;

FeP(CF$_3$)$_4$, meso-tetra(trifluoromethyl)porphyrinato iron;

FeP(CF$_3$)$_2$, meso-bis(trifluoromethyl)porphyrinato iron;

Fe[(TPFPP)$_2$(CF$_3$)$_2$-β-Br$_8$]Cl, meso-(5,15)-bis(pentafluorophenyl)-meso-(10,20)-bis(trifluoromethyl)-β-octabromoporphyrinato iron(III)chloride;

Fe[P(CF$_3$)$_4$Br$_8$]Cl, meso-tetrakis (trifluoromethyl) β-octabromo porphyrinato iron(III)chloride; and FePCl$_{12}$, meso-tetrachloro-β-octachloro porphyrinato iron.

In the above, "P" is porphyrin, "meso" is one or more of the 5, 10, 15 and 20 positions of the porphyrin ring, "β"is one or more of the 2, 3, 7, 8, 12, 13, 17 and 18 positions of the porphyrin molecule, "tetra" as used in connection with "meso" indicates four substituents, one on each of the four pyrrolic rings of the porphyrin molecule, "TPP" is tetraphenylporphyrin, "TPFPP" is tetra(pentafluorophenyl) porphyrin, and X is halogen.

PHTHALOCYANINE CATALYSTS

Phthalocyanines may be defined, for example, as compounds comprising four isoindole rings joined in a 16-membered ring of alternating carbon and nitrogen atoms around a central metal atom. R. Grant et al., supra. Any metal phthalocyanine catalyst for oxidation of alkanes may be used in the method according to the invention; for example, such catalysts include:

FePcCl, phthalocyanato iron chloride;

[Fe(Pc)]$_2$N, bis-phthalocyanato iron(III) nitride;

Mn(Pc)N$_3$, phthalocyanato manganese azide;

Fe(FPc)Cl, perfluorophthalocyanato iron chloride;

Na[Fe(FPc)(N$_3$)$_2$], perfluorophthalocyanato iron sodium diazide;

Fe(FPc)N$_3$ perfluorophthalocyanato iron azide;

Fe(ClPc)Cl, perchlorophthalocyanato iron chloride;

Fe[(tBu)$_4$Pc]Cl, tetra(t-butyl)phthalocyanato iron chloride.

In the above, "Pc" is the phthalocyanine ring, "tBu" is tertiary butyl, and F and Cl are perfluoro and perchloro, respectively.

ACETYLACETONATE CATALYSTS

Acetylacetonates may be defined, for example, as chelates of acetylacetone coordinated with a metal. R. Grant et al., supra. Any metal acetylacetonate catalyst for oxidation of alkanes may be used in the method according to the invention; for example, such catalysts include Co(acac)$_2$, cobalt acetylacetonate; and Ru(acac)$_3$, ruthenium acetylacetonate. In the above, "acac" is the acetylacetonate ligand. In addition to cobalt and ruthenium, suitable metals include iron, manganese and chromium.

PRESENCE OF A BASE

The reaction according to the invention is carried out in the presence of a base, for example an alkali metal or alkaline earth metal hydroxide, a basic ion exchange resin or the like. Alkali metal compounds are preferred bases for use according to the invention. Such compounds may comprise compounds of sodium, potassium, cesium, rubidium, lithium or francium, or mixtures thereof. The base may also be an alkaline earth metal such as calcium, magnesium, barium, strontium or mixtures thereof or a basic ion exchange resin. The strength of said base is preferably equivalent to about 2 to about 12 normal sodium hydroxide, more preferably equivalent to about 6 to about 10 normal sodium hydroxide.

The beneficial effect of the addition of base in the reaction results in cost savings since more alkane can be reacted in a single pass without additional catalyst. This is due to the higher reaction rates achieved by the process of the invention.

REACTION MIXTURE

The reaction mixture of the method according to the invention contains an organic compound feedstock, a metal organic ligand catalyst, oxygen and a base, and may be carried out in any suitable medium, but is preferably carried out in homogeneous liquid phase. Preferably the amount of base in the reaction mixture is in the range from about 1 to about 9 parts by weight per 100 parts by weight of the organic compound, more preferably in the range from about 3 to about 7 parts by weight per 100 parts by weight of the organic compound.

REACTION CONDITIONS

Any suitable temperature and pressure may be used in the partial oxidation of organic compounds by the method of the invention. Preferably the temperature is in the range from 25 to 250° C., more preferably 70 to 180° C., and the pressure in the range from 15 to 1500 psig, more preferably 30 to 750 psig.

DESCRIPTION OF THE DRAWING

FIG. 1 is a graphical comparison of the method according to the invention, in which the reaction mixture contains a base, as compared with otherwise similar operation in which a base was not added to the reaction mixture.

EXAMPLES

The following examples illustrate the invention:

Example 1

Isobutane oxidation was carried out in liquid phase at 80° C. and 45 psia O$_2$ partial pressure. Typical isobutane charge was 120–140 grams. In FIG. 1 is shown conversion of isobutane as a function of time (a) in the presence of 40 mg meso-tetra(pentafluorophenyl)-β-octachloro-porphyrin hydroxide, Fe(TPFPP)Cl$_8$OH, catalyst, and (b) in the presence of 40 mg Fe(TPFPP)Cl$_8$OH catalyst and 5 ml of 8N NaOH. In the presence of catalyst only, (a), the reaction proceeded rapidly initially, but came to a halt at final conversion of 36% in 6 hours. In the second reaction, (b), where NaOH was added, the reaction rate was slower initially, but improved with time. The conversion of isobutane at 6 hours was the same as in the previous case, but the final conversion of isobutane was 54% after 16 hours in the presence of NaOH.

In further experiments using 1N or lower strength NaOH, lower final conversions of isobutane were obtained than in the above experiment with 8N NaOH. Preferably the strength of the base used is in the range from about 2 to about 12N. Stronger base strength than about 12N is undesirable because it may cause deterioration of the catalyst.

Example 2

Isobutane was oxidized using 28 mg Fe(TPFPP)Cl$_8$OH, also known as Fe[PPF$_{20}$Cl$_8$]OH, catalyst per 100 g at 80° C. and 45 psia O$_2$, with varying amounts of 8N NaOH. The results are shown in Table I below.

Both base strength and base concentration in the reaction mixture have an impact on conversion in oxidation reactions as shown in Table I and Table II. For examples, using 9.90 g/100 g of 8N NaOH resulted in lower conversion and lower TBA yield than using 4.97 g/100 g of 8N NaOH. Selectivity for the desired product, tert-butylalcohol, in both reactions was about 80% based on gas chromatographic analyses. Due to the effects of base strength and base concentration, it is within the ability of the skilled practitioner to adjust reaction parameters to achieve desired conditions and outcomes.

TABLE I

| Run | Catalyst (mole cat/mole iC$_4$ 10$^5$) | NaOH Amount g/100 g | Conversion % | TBA % | Time min |
| --- | --- | --- | --- | --- | --- |
| 1 | 1.29 | 0.00 | 36 | 30 | 370 |
| 2 | 1.43 | .066 | 40 | 32 | 580 |
| 3 | 1.40 | 4.97 | 54 | 44 | 954 |
| 4 | 1.35 | 9.90 | 44 | 36 | 780 |

Example 3

Isobutane was oxidized under the same conditions as in Example 2, except that the strength of the NaOH was varied from run to run. The amount of base added was 0.6 g NaOH solution per 100 g reaction mixture. Table II shows the results:

TABLE II

| Run | Catalyst (mole cat/mole iC$_4$ 10$^5$) | NaOH Strength N | Conversion % | TBA & | Time Min |
| --- | --- | --- | --- | --- | --- |
| 5 | 1.24 | 0.00 | 32 | 26 | 380 |
| 6 | 1.27 | 1.6 | 30.6 | 25.3 | 360 |
| 7 | 1.43 | 8.0 | 40 | 32 | 580 |
| 8 | 1.20 | Pellets | 5.5 | 4.7 | 207 |

Run 7, representing the same data as Run 2 in Table I, is included again in Table II to show more clearly the effect of changing NaOH strength. In Run 8, 4 g dry NaOH pellets were added, and water was produced as the reaction proceeded. The base strength in Run 8 is believed to have exceeded 20N NaOH and the reaction essentially ceased after one hour.

The invention claimed is:

1. Method for partial oxidation of alkanes to alkanols which comprises contacting an alkane with a metal organic ligand catalyst in the presence of an inorganic base.

2. Method according to claim 1 wherein said metal is a transition metal.

3. Method according to claim 2 wherein said catalyst comprises a transition metal complex of a ligand selected from the group consisting of porphyrins, phthalocyanines, porphenes, porphycenes, 1,3-bis(arylimino)-isoindolines, acetates, Schiff bases, mono-, bi-, tri- and tetradentate systems, acetylacetonates, naphthenates, propanates, butyrates, benzoates, stearates, bipyridines, terpyridines, phenanthrolines, dithiocarbamates, xanthates, salicylaldimines, cyclam, dioxycyclams, pyrazoylborates, and tetraazamacrocycles.

4. Method according to claim 2 wherein said ligand is a porphyrin.

5. Method according to claim 4 wherein said porphyrin contains one or more electron-withdrawing atoms or groups in meso and/or beta positions.

6. Method according to claim 5 wherein said atoms or groups are selected from the group consisting of halogen, nitro, cyano, halocarbyl, nitrocarbyl and cyanocarbyl atoms or groups.

7. Method according to claim 6 wherein said ligand is a perhaloporphyrin.

8. Method according to claim 7 wherein said metal is selected from the group consisting of iron, cobalt, chromium, manganese, ruthenium and copper.

9. Method according to claim 8 wherein said metal is iron.

10. Method according to claim 2 wherein said ligand is a phthalocyanine.

11. Method according to claim 10 wherein said phthalocyanine contains one or more electron-withdrawing atoms or groups.

12. Method according to claim 11 wherein said atoms or groups are selected from the group consisting of halogen, nitro, cyano, halocarbyl, nitrocarbyl and cyanocarbyl atoms or groups.

13. Method according to claim 12 wherein said metal is selected from the group consisting of iron, cobalt, chromium, manganese, ruthenium and copper.

14. Method according to claim 2 wherein said ligand is acetylacetonate.

15. Method according to claim 14 wherein said metal is selected from the group consisting of iron, cobalt, chromium, manganese and ruthenium.

16. The method according to claim 15 wherein said metal comprises cobalt.

17. The method according to claim 15 wherein said metal comprises ruthenium.

18. Method according to claim 1 wherein said base is an alkali metal compound.

19. Method according to claim 18 wherein said alkali metal is sodium.

20. Method according to claim 18 wherein said alkali metal is potassium.

21. Method according to claim 1 wherein said base is an alkaline earth metal compound.

22. Method according to claim 21 wherein said alkaline earth meal is calcium.

23. Method according to claim 1 wherein said base is a basic ion exchange resin.

24. Method according to claim 1 wherein said alkane is isobutane.

25. Method according to claim 1 wherein the strength of said base is equivalent to about 2 to about 12 normal sodium hydroxide.

26. Method according to claim 25 wherein said strength is equivalent to about 6 to about 10 normal sodium hydroxide.

27. Method according to claim 1 wherein the amount of said base is in the range from about 1 to about 9 parts by weight per 100 parts by weight of said alkane.

28. Method according to claim 27 wherein said amount is in the range from about 3 to about 7 parts by weight per 100 parts by weight of said alkane.

* * * * *